(12) United States Patent  
Iguchi

(10) Patent No.: US 8,523,842 B2  
(45) Date of Patent: Sep. 3, 2013

(54) DUAL-LUMEN CATHETER WITH CONTRASTRADIOGRAPHY SECTIONS TO IDENTIFY THE LUMENS

(75) Inventor: Masanobu Iguchi, Fukuroi (JP)

(73) Assignee: Covidien AG (CH)

( * ) Notice: Subject to any disclaimer, the term of this patent is extended or adjusted under 35 U.S.C. 154(b) by 859 days.

(21) Appl. No.: 11/664,307

(22) PCT Filed: Oct. 4, 2005

(86) PCT No.: PCT/EP2005/010676  
§ 371 (c)(1),  
(2), (4) Date: Nov. 16, 2007

(87) PCT Pub. No.: WO2006/037608  
PCT Pub. Date: Apr. 13, 2006

(65) Prior Publication Data  
US 2008/0195063 A1    Aug. 14, 2008

(30) Foreign Application Priority Data  
Oct. 1, 2004 (JP) .................................. 2004-290209

(51) Int. Cl.  
*A61M 25/098* (2006.01)

(52) U.S. Cl.  
USPC ........................................................ 604/529

(58) Field of Classification Search  
USPC ...................... 604/529, 103.1, 264; 623/1.34  
See application file for complete search history.

(56) References Cited

U.S. PATENT DOCUMENTS

| 4,469,483 | A | * | 9/1984 | Becker et al. ................. 604/529 |
| 5,289,831 | A | * | 3/1994 | Bosley .......................... 128/899 |
| 5,451,206 | A |   | 9/1995 | Young |
| 5,542,937 | A | * | 8/1996 | Chee et al. .................... 604/523 |
| 6,200,338 | B1 | * | 3/2001 | Solomon et al. ............. 623/1.34 |

FOREIGN PATENT DOCUMENTS

| CN | 1260211 A | 7/2000 |
| FR | 2 530 958 A | 2/1984 |

OTHER PUBLICATIONS

Office Action issued in corresponding Chinese Patent Application No. 200580041146.X dated Jun. 5, 2009.

* cited by examiner

*Primary Examiner* — Kevin C Sirmons  
*Assistant Examiner* — Bradley Osinski  
(74) *Attorney, Agent, or Firm* — John Paul Mello, Esq.

(57) ABSTRACT

A catheter has an outer peripheral portion (15) in the form of a tube and an internal wall (16, 26) within the tube forming a plurality of lumens (11*a*, 11*b*, 21*a*, 21*b*). Axially extending linear contrastradiography sections (17*a*, 17*b*, 27*a*, 27*b*) of radiopaque material are formed at a plurality of intersection points between the outer peripheral section and the wall, the peripheral extent (a, b) of the respective contrastradiography sections being different.

20 Claims, 3 Drawing Sheets

DUAL-LUMEN CATHETER WITH CONTRASTRADIOGRAPHY SECTIONS TO IDENTIFY THE LUMENS

This application is a 371 of PCT/EP05/010676, filed Oct. 4, 2005.

BACKGROUND

1. Technical Field

The present invention relates to a catheter for placement in a blood vessel to supply a medicinal fluid or a nutritional supplement to a patient.

2. Description of Related Art

It is well known to provide a person (hereinafter referred to as a patient) with decreased oral ingestion function, for example due to old age or disease, with a medicinal fluid or a nutritional supplement for a high-calorie infusion through a blood vessel by means of a catheter. It is known to confirm the position of the catheter by incorporating a radiopaque agent (see, for example, JP-U-51 108 389). Such a catheter is formed of a flexible plastic tube and has a section which extends in the axial direction of the plastic tube and which incorporates a radiopaque agent. The radiopaque agent conventionally extends in a circumferential direction around the wall of the plastic tube. Therefore, in a situation where the catheter has been placed in a blood vessel of the patient, the position of the catheter can be confirmed by irradiating X-rays to form an image of the radiopaque agent.

Included among these catheters are double lumen catheters which have two lumens, that is a main lumen and a sublumen, to supply different medicinal fluids through the respective lumens, and also catheters having more than two lumens. However, in such catheters, when the thickness of the section incorporating the radiopaque agent is small, it is difficult to confirm the position of the catheter because the radiographic contrast is reduced. Therefore, in order to improve the radiographic contrast for detecting the radiopaque agent, it is necessary to increase the cross-sectional area (thickness) of the section incorporating the radiopaque agent. However, when the cross-sectional area of the section incorporating the radiopaque agent is increased, there are problems in that the strength of the catheter is reduced, and it is difficult to confirm that the medicinal fluids are passing through the catheter.

Further, it has been proposed for double lumen catheters to incorporate a narrow section incorporating radiopaque agent at two different regions corresponding to the main lumen and the sublumen. However, in this case, it is difficult to distinguish between the main lumen and the sublumen so that the effectiveness is reduced at the time when the catheter is assembled during manufacture. Specifically, during manufacture of the catheter, even though different members, such as adapters, are connected to the main lumen and the sublumen, it is difficult to distinguish between the main lumen and the sublumen and the operation is laborious.

It is an object of the present invention to provide a catheter which improves the effectiveness of contrastradiography and which, at the same time, does not reduce the effectiveness at the time when the catheter is manufactured.

SUMMARY

According to the present invention there is provided a catheter having an outer peripheral portion in the form of a tube and an internal wall within the tube forming a plurality of lumens, wherein axially extending linear contrastradiography sections of radiopaque material are formed at a plurality of intersection points between the outer peripheral section and the wall, the peripheral extent of the respective contrastradiography sections being different.

Because the contrastradiography sections are formed at the plurality of intersection points, the contrastradiographic property can be improved due to the plurality of the contrastradiography sections. Further, because the peripheral extent (width) of the respective contrastradiography sections is different, it is possible to distinguish the respective lumens corresponding to the contrastradiography sections. The different peripheral extent of the contrastradiography sections can readily be effected during manufacture and the ease of use of the catheter can be improved. Furthermore, since the contrastradiography sections are formed at the intersection points of the outer peripheral sections and the wall, the passage of medicinal fluids through the catheter can readily be confirmed. In particular in the case where more than two lumens are provided, the contrastradiography sections need not be formed at all of the intersection points, but at only selected intersection points.

A single internal wall may be provided so as to form two lumens with first and second contrastradiography sections, the ratio of the peripheral extent of one of the first and second sections to the peripheral extent of the other of the first and second sections being in the range from 1:3 to 2:3. In one embodiment of the invention the ratio may be substantially 1:2.

In this way it is possible to correctly distinguish between the two contrastradiography sections so as to easily discriminate the respective lumens. Further, by setting the ratio of the peripheral extent of the two linear contrastradiography sections to the above values, a catheter can be obtained, the location of which can be determined with precision and through which the passage of medicinal fluids can be confirmed.

In at least one of the contrastradiography sections the radiopaque material extends into the wall. A contrastradiography section may be formed within the wall.

In this case, the radiographic contrast of the catheter with respect to X-rays is improved, while the passage of medicinal fluids through the lumens can readily be confirmed.

A further linear contrastradiography section may be formed solely within the outer peripheral section.

The radiopaque material may be wholly embedded within the catheter.

Therefore, since the radiopaque material is not exposed, deterioration or stripping can be avoided. For example, in the event that the contrastradiography section is formed of a mixture of barium sulfate and a polyurethane resin, any exposed material deteriorates as a result of contact with alcohol.

BRIEF DESCRIPTION OF THE DRAWINGS

For a better understanding of the present invention and to show more clearly how it may be carried into effect reference will now be made, by way of example, to the accompanying drawings in which.

DETAILED DESCRIPTION OF THE EMBODIMENTS

Figure 1:
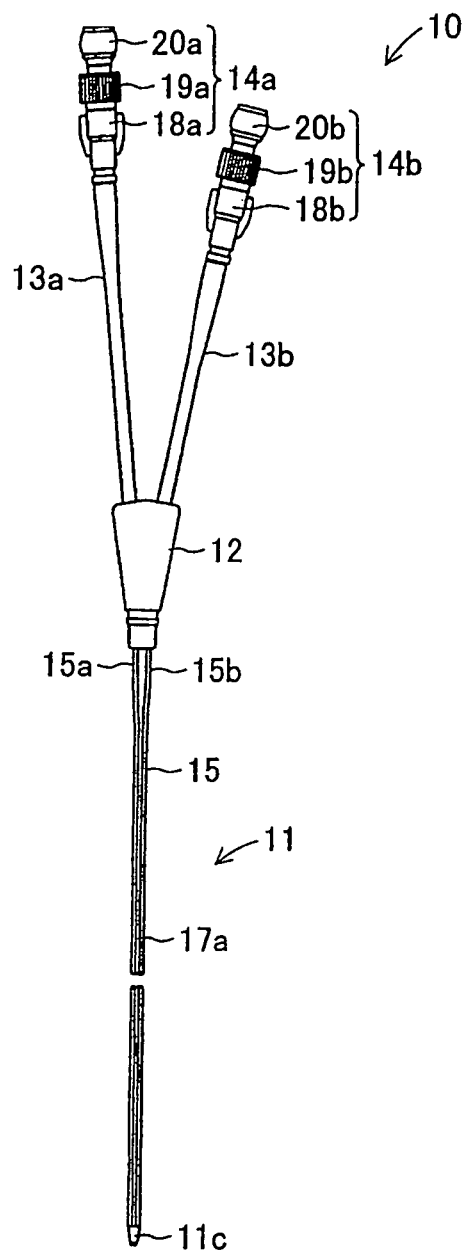
FIG. 1 is a plan view of a double lumen catheter according to a first embodiment of the present invention.

A first embodiment of the catheter according to the invention will now be explained with reference to accompanying drawings. FIG. 1 shows a double lumen catheter 10 which includes a catheter main body 11 formed of a long flexible tube, a connecting member 12, a pair of connecting tube members 13a and 13b which are formed of flexible tubes, and a pair of lure adapters 14a and 14b.

Figure 2:
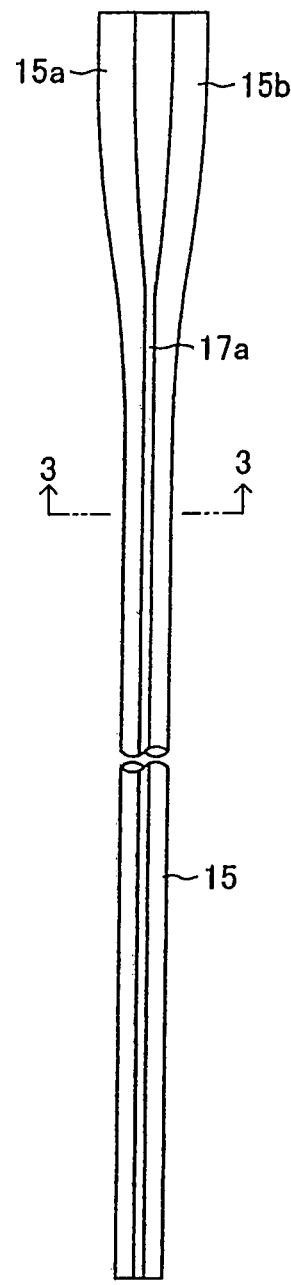
FIG. 2 is a plan view of a catheter main body of the double lumen catheter shown in FIG. 1.
Figure 3:
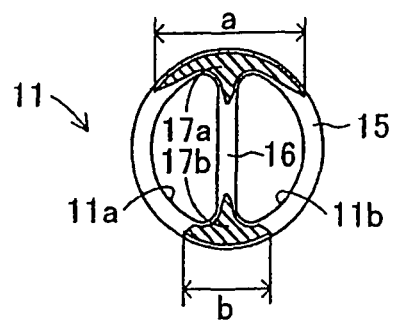
FIG. 3 is a cross-sectional view taken along the line 3-3 of FIG. 2.

The catheter main body 11 is formed of a soft polyurethane resin and, as shown in FIGS. 2 and 3, is in the form of a tube having a cylindrical outer peripheral section 15 with a substantially diametrically extending wall 16 to divide the outer peripheral section 15 internally into two parts. The wall 16 forms two lumens, a main lumen 11a and a sublumen 11b, within the outer peripheral section 15. Where the outer peripheral section 15 and the wall 16 intersect, linear contrastradiography sections 17a and 17b, of contrastradiographic material, are provided in the catheter body so as to extend in the longitudinal direction of the catheter main body 11.

A mixture of white barium sulfate and a polyurethane resin is employed in that part of the polyurethane resin in the linear contrastradiography sections 17a and 17b in such a manner that the barium sulfate is not exposed at the surfaces of the outer peripheral section 15 or of the wall 16. The width a of a portion of the linear contrastradiography section 17a along the outer peripheral section 15 is set to be larger than the width b of a portion of the linear contrastradiography section 17b along the outer peripheral section 15. The ratio of the width a of the linear contrastradiography section 17a to the width b of the linear contrastradiography section 17b is set to be approximately 1:2. Further, inner central portions of both linear contrastradiography sections 17a and 17b protrude a short distance internally of the wall 16 (the center of the outer peripheral section 15).

A leading end of the catheter main body 11 is provided with an opening 11c having a tapered outer peripheral surface, and a rear end of the catheter body 11 is divided into a main outer peripheral section 15a and a sub outer peripheral section 15b which are separated from each other in order to separate the main lumen 11a and the sublumen 11b. Therefore, a rear end of the main peripheral section 15a and a rear end of the sub peripheral section 15b can be connected to connecting tube members 13a and 13b by means of a connecting member 12, respectively.

The connecting tube members 13a and 13b are in the form of tubes which are made of a soft polyurethane resin and the outer diameters of which are larger than that of the catheter main body 11. In order to distinguish the connecting tube members 13a and 13b, the connecting tube member 13a is blue, and the connecting tube member 13b is colorless. Further, the connecting member 12 is formed of a soft polyurethane resin, and has a connection portion which is secured around the connection portion of the main peripheral section 15a and the sub peripheral section 15b and also around the connecting tube members 13a and 13b.

The connecting member 12 is substantially triangular in shape, a portion connected with the main peripheral section 15a and the sub peripheral section 15b being relatively narrow, and a portion connected with the connecting tube members 13a and 13b being relatively wide. Pathways are formed in the connecting member 12 to connect the main peripheral section 15a with the connecting tube member 13a and to connect the sub peripheral section 15b with the connecting tube member 13b.

The lure adapters 14a and 14b are made polyurethane resin and have the same structure. The lure adapter 14a includes a tube fixing section 18a, a grasping section 19a, and a medicinal fluid injecting section 20a, while the lure adapter 14b includes a tube fixing section 18b, a grasping section 19b, and a medicinal fluid injecting section 20b. The tube fixing section 18a is fixed to the rear end of the connecting tube member 13a, and the tube fixing section 18b is fixed to the rear end of the connecting tube member 13b.

The grasping sections 19a and 19b are detachably attached to the tube fixing sections 18a and 18b by way of screw-threaded portions (not shown), respectively. When an operator manipulates the double lumen catheter 10, he can grasp the grasping sections 19a and 19b. Further, the medicinal fluid injecting sections 20a and 20b are fixed to the grasping sections 19a and 19b, respectively and have a soft elastomer attached thereto. When supplying the medicinal fluid into the double lumen catheter 10, an injecting section of an infusion line (not shown) is inserted into the elastomer of the medicinal injecting sections 20a and 20b to inject the medicinal fluid. Furthermore, since the medicinal fluid passes through the double lumen catheter 10, in order to see the medicinal fluid therein, portions other than the lure adapters 14a and 14b are formed of transparent materials.

As mentioned above, when supplying two kinds of medicinal fluids into a body of a patient through a blood vessel (not shown) using the double lumen catheter 10, firstly a cannula punctures the blood vessel. Thereafter, the opening 11c formed at the leading end of the double lumen catheter 10 is inserted into the cannula that is already placed in the blood vessel so as to be placed into a target position in the blood vessel. Thereafter, when the opening 11c of the double lumen catheter 10 reaches the target position, the cannula is removed from the blood vessel. During that time, it is required to be able to prevent deviation of the double lumen catheter 10 and to confirm that the opening 11c of the double lumen catheter is at the target position. Since the linear contrastradiography sections 17a and 17b are formed of a material which does not transmit X-rays, confirmation is performed by forming an image.

After the double lumen catheter 10 is placed in the blood vessel, the medicinal fluid injecting sections 20a and 20b are connected to a predetermined infusion line to begin injecting the medicinal fluid. Thus the medicinal fluids enter the body of the patient through the blood vessel. In this case, since the linear contrastradiography sections 17a and 17b occupy a small portion of the outer peripheral section 15 of the catheter main body 11, it is possible to confirm that the medicinal fluids are passing through the main lumen 11a and the sublumen 11b. In this case, confirmation that the medicinal fluids can be accomplished by viewing a portion of the outer peripheral section 15 of the catheter main body 11 which is located externally of the patient's body.

During manufacture of the double lumen catheter 10, the linear contrastradiography sections 17a and 17b are formed with different widths so as to function as differentiating markers. In this way, the connection of the main outer peripheral section 15a to the connecting tube member 13a and the connection of the sub outer peripheral section 15b to the connecting tube member 13b are satisfactorily performed. Further, the connection of the connecting tube members 13a and 13b to the lure adapters 14a and 14b is also satisfactorily performed. Therefore, it is possible to improve the effectiveness of the catheter.

As mentioned above, since in the double lumen catheter 10 the linear contrastradiography sections 17a and 17b are formed at intersection points of the outer peripheral section 15 and the wall 16 of the catheter main body 11, it is possible to confirm the position of the double lumen catheter 10 by radiography. Further, in this case, since the widths of the linear contrastradiography sections 17a and 17b are different from each other, it is possible to distinguish the main lumen 11a and the sublumen 11b on the basis of the difference.

Furthermore, because the linear contrastradiography sections 17a and 17b are formed only at the intersection points of the outer peripheral section 15 and the wall 16, it is readily possible to confirm that medicinal fluids are passing through the main lumen 11a and the sublumen 11b, respectively. Because the linear contrastradiography sections 17a and 17b are arranged within the outer peripheral section 15 not to be exposed at the surface thereof, it is further possible to prevent deterioration or stripping thereof. Therefore, the useful life of the double lumen catheter 10 can be increased.

Figure 4:
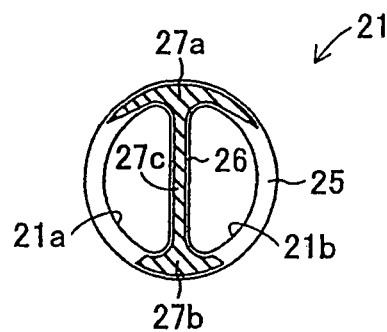
FIG. 4 is a cross-sectional view of a catheter main body of a double lumen catheter according to a second embodiment of the present invention.

FIG. 4 shows a section through a catheter main body of double lumen catheter according to a second embodiment of the invention. In this catheter main body 21, a linear contrastradiography section 27c is additionally formed in a wall 26. The linear contrastradiography section 27c is integrally connected to the linear contrastradiography sections 27a and 27b which are formed at the intersection points of an outer peripheral section 25 and the wall 26. Therefore, due to the wall 26 two lumens, in the form of a main lumen 21a and a sublumen 21b, are formed in the catheter main body 21. The remaining structure of the double lumen catheter is similar to the double lumen catheter 10 described above in relation to FIGS. 1 to 3.

According to the double lumen catheter of FIG. 4, it is possible more readily to confirm the position of the catheter main body 21 and to distinguish between the main lumen 21a and the sublumen 21b. Further, it remains possible readily to confirm that medicinal fluids are passing through the main lumen 21a and the sublumen 21b. The other effects of the double lumen catheter are similar to the double lumen catheter 10 described above in relation to FIGS. 1 to 3.

Further, the catheter according to the present invention is not limited to the above-described embodiments, and appropriate modifications may be made. For example, in the above embodiments, even though the ratio of the width a of the linear contrastradiography section 17a to the width b of the linear contrastradiography section 17b and the ratio of the width a of the linear contrastradiography section 27a to the width b of the linear contrastradiography section 27b are set to be approximately 1:2, the ratio is not limited thereto, and may be changed. In this case, the width ratio of the respective linear contrastradiography sections can be set to any suitable predetermined value, preferably in the range from 1:3 to 2:3.

Furthermore, the present invention is not limited to use in double lumen catheters, but can be used in other multi-lumen catheters, such as triple lumen catheters or catheters incorporating more than three lumens. In this case, the linear contrastradiography sections do not need to be provided at all of the intersection points of the outer peripheral section and the wall, but can be provided at selected intersection points.

The linear contrastradiography sections 17a and 17b extend partly around outer peripheral section 15 and partly within the wall 16 in the first embodiment, and the linear contrastradiography sections 27a, 27b, and 27c extend partly around the outer peripheral section 15 and the entire extent of the wall 16 in the second embodiment. However, the linear contrastradiography sections need only be formed in the outer peripheral section 15. In this case, the linear contrastradiography section 27c is not provided. Further, it may be preferable that one of the linear contrastradiography sections, for example the linear contrastradiography section 17a, is formed in both the outer peripheral section 15 and the wall 16, and the other linear contrastradiography section 17b is formed only in the outer peripheral section 15. Furthermore, in a catheter having three or more lumens, it may be preferable that one linear contrastradiography section is formed in both the outer peripheral section and the wall, and the remaining linear contrastradiography sections are formed only in the outer peripheral section.

In the above-described embodiments, even though the main lumen 11a and the sublumen 11b, and the main lumen 21a and the sublumen 21b, have substantially same size, the sizes of the lumens and sublumens may be determined appropriately. For example, the main lumen may have a relatively large cross-sectional area, and the sublumen may have a relatively small cross-sectional area. Further, the shape or the size of the respective linear contrastradiography sections, and the material, the shape, and the size of the members forming the respective sections of the catheter may be appropriately modified.

The invention claimed is:

1. A catheter, which comprises:
a catheter main body including an outer peripheral section and an internal wall having a first end and a second end, the catheter main body defining first and second lumens extending along a longitudinal axis of the catheter main body, wherein the first and second ends of the internal wall each intersect the peripheral section of the catheter main body at a respective first intersection area and a respective second intersection area; and
first and second contrastradiography sections disposed at least within the outer peripheral section and the first and second intersection areas, the first and second contrastradiography sections defining respective first and second different peripheral extents, and being positioned to assist in distinguishing the first lumen from the second lumen during imaging of the catheter main body.

2. The catheter according to claim 1 wherein the first and second contrastradiography sections are each dimensioned to at least partially extend into the internal wall.

3. The catheter according to claim 1 wherein the outer peripheral section includes an outer surface, the first and second contrastradiography sections being disposed adjacent areas of intersection between outer surface of the outer peripheral section and the internal wall.

4. The catheter according to claim 3 wherein the first and second contrastradiography sections are disposed in general diametrically opposed relation.

5. The catheter according to claim 4 wherein the ratio of the width of the first peripheral extent of the first contrastradiography section to the second peripheral extent of the second contrastradiography sections ranges from about 1:3 to about 2:3.

6. The catheter according to claim 5 wherein the ratio of the first peripheral extent of the first contrastradiography section to the second peripheral extent of the second contrastradiography is about 1:2.

7. The catheter according to claim 1 wherein the internal wall includes a contrastradiography section.

8. The catheter according to claim 7 wherein the contrastradiography section of the internal wall is dimensioned to extend an entire extent of the internal wall.

9. The catheter according to claim 1 wherein the first and second contrastradiography sections are dimensioned to extend in a substantially linear manner along an axial portion of the catheter main body.

10. A catheter, which comprises:
a catheter main body including an outer peripheral section and an internal wall extending within the outer peripheral section to define first and second lumens along a longitudinal axis of the catheter main body, the internal wall having a first end and a second end, the first and second ends of the internal wall each intersecting the outer peripheral section of the catheter main body at respective first and second intersection areas; and
first and second contrastradiography sections at least partially embedded within the catheter main body adjacent the first and second intersection areas and the internal wall, the first and second contrastradiography sections having different peripheral extents and being positioned to assist in distinguishing the first lumen from the second lumen during imaging of the catheter main body.

11. The catheter according to claim 10 wherein the first and second contrastradiography sections are each dimensioned to at least partially extend into the internal wall.

12. The catheter according to claim 10 wherein the internal wall includes a contrastradiography section at least partially embedded therein.

13. The catheter according to claim 12 wherein the contrastradiography section of the internal wall is dimensioned to extend an entire extent of the internal wall.

14. The catheter according to claim 10 wherein the first and second contrastradiography sections are dimensioned to extend in a substantially linear manner along an axial portion of the catheter main body.

15. A catheter, which comprises:
a catheter main body including an outer peripheral section and an internal wall having a first end and a second end, the catheter main body defining first and second lumens extending along a longitudinal axis of the catheter main body, wherein the first and second ends of the internal wall each intersect the peripheral section of the catheter main body at a respective first intersection area and a respective second intersection area; and
a first contrastradiography section disposed at least within the outer peripheral section and a first portion of the internal wall located adjacent the first intersection area, the first contrastradiography section defining a first peripheral extent,
a second contrastradiography section disposed at least within the outer peripheral section and a second portion of the internal wall located adjacent the second intersection area, the second contrastradiography section defining a second peripheral extent;
wherein the first and second peripheral extents are different and are positioned and configured to assist in distinguishing the first lumen from the second lumen during imaging of the catheter main body.

16. The catheter according to claim 15, wherein the ratio of the first peripheral extent of the first contrastradiography section to the second peripheral extent of the second contrastradiography sections ranges from about 1:3 to about 2:3.

17. The catheter according to claim 15, wherein the contrastradiography section of the internal wall is dimensioned to extend an entire extent of the internal wall.

18. A catheter, which comprises:
a catheter main body including an outer peripheral section and an internal wall extending within the outer peripheral section to define first and second lumens along a longitudinal axis of the catheter main body, the internal wall having a first end and a second end, the first and second ends of the internal wall each intersecting the outer peripheral section of the catheter main body at respective first and second intersection areas; and
first and second contrastradiography sections at least partially embedded within the outer peripheral section of the catheter main body and portions of the internal wall located adjacent the first and second intersection areas, the first and second contrastradiography sections having different peripheral extents and being positioned and configured to assist in distinguishing the first lumen from the second lumen during imaging of the catheter main body.

19. The catheter according to claim 18, wherein the ratio of the first peripheral extent of the first contrastradiography section to the second peripheral extent of the second contrastradiography sections ranges from about 1:3 to about 2:3.

20. The catheter according to claim 18, wherein the contrastradiography section of the internal wall is dimensioned to extend an entire extent of the internal wall.

* * * * *